US010222382B2

(12) United States Patent
De Faire et al.

(10) Patent No.: US 10,222,382 B2
(45) **Date of Patent: *Mar. 5, 2019**

(54) PHOSPHORYLCHOLINE CONJUGATES AND CORRESPONDING ANTIBODIES

(71) Applicant: Athera Biotechnologies AB, Stockholm (SE)

(72) Inventors: Ulf De Faire, Taby (SE); Johan Frostegård, Stockholm (SE)

(73) Assignee: ATHERA BIOTECHNOLOGIES AB, Stockholm (SE)

( * ) Notice: Subject to any disclaimer, the term of this patent is extended or adjusted under 35 U.S.C. 154(b) by 1127 days.

This patent is subject to a terminal disclaimer.

(21) Appl. No.: 14/155,903

(22) Filed: Jan. 15, 2014

(65) Prior Publication Data

US 2014/0186360 A1 Jul. 3, 2014

Related U.S. Application Data

(62) Division of application No. 13/208,138, filed on Aug. 11, 2011, which is a division of application No. 10/599,934, filed as application No. PCT/GB2005/001463 on Apr. 15, 2005, now Pat. No. 8,012,483.

(60) Provisional application No. 60/521,384, filed on Apr. 15, 2004.

(51) Int. Cl.

*A61K 39/395* (2006.01)
*G01N 33/68* (2006.01)
*C07K 16/18* (2006.01)
*C07K 16/44* (2006.01)
*A61K 47/64* (2017.01)

(52) U.S. Cl.

CPC ... *G01N 33/6854* (2013.01); *A61K 39/39583* (2013.01); *A61K 47/646* (2017.08); *C07K 16/18* (2013.01); *C07K 16/44* (2013.01); *G01N 33/6893* (2013.01); *C07K 2317/52* (2013.01); *G01N 2800/323* (2013.01); *G01N 2800/50* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 4,203,893 A | 5/1980 | Pery et al. |
| 5,455,032 A | 10/1995 | Kenny |
| 5,475,100 A | 12/1995 | Hashino et al. |
| 5,702,727 A | 12/1997 | Amkraut |
| 5,955,584 A | 9/1999 | Ditlow et al. |
| 6,375,925 B1 | 4/2002 | Tsimikas et al. |
| 6,780,605 B1 | 8/2004 | Frostegård |
| 8,236,562 B2 | 8/2012 | Schuler et al. |
| 2004/0185039 A1 | 9/2004 | Kohler |
| 2004/0185514 A1 | 9/2004 | Frostegård |
| 2004/0185515 A1 | 9/2004 | Frostegård |
| 2004/0185516 A1 | 9/2004 | Frostegård |
| 2007/0122419 A1 | 5/2007 | Witztum et al. |

FOREIGN PATENT DOCUMENTS

| | | |
|---|---|---|
| CN | 1471575 A | 1/2004 |
| EP | 0257778 | 3/1988 |
| EP | 0466505 | 1/1992 |
| EP | 1095271 | 5/2001 |
| EP | 1335742 | 8/2003 |
| JP | 02188532 | 7/1990 |
| WO | WO 90/12632 | 11/1990 |
| WO | WO 92/10203 | 6/1992 |
| WO | WO 93/18161 | 9/1993 |
| WO | WO 94/14454 | 7/1994 |
| WO | WO 98/21581 | 5/1998 |
| WO | WO 99/08109 | 2/1999 |
| WO | WO 99/33522 | 7/1999 |
| WO | WO 00/02046 | 1/2000 |
| WO | WO 01/32070 | 5/2001 |
| WO | WO 01/68119 | 9/2001 |

(Continued)

OTHER PUBLICATIONS

"Assessment and prevention of inflammatory risk in cardiovascular disease," *Athera Biotechnologies*, Company Profile, Oct.-Dec. 2004.
"Biofluids," Product information from Asterand, available online at http://www.asterand.com/Asterand/human_tissues/biofluids.htm, 2009.
"Biofluids," Product information from ProteoGenex, available online at http://www.proteogenex.com/Biorepository/Biofluids.html, 2009.
"History of Framingham Heart Study, " available online at http://www.framinghamheartstudy.org/about/history.html, accessed Dec. 11, 2008.
"Human Derived Products," Product information from Source Bio, Inc., available at http://sourcebioinc.homestad.com/human-derived-products.html, 2008.

(Continued)

*Primary Examiner* — Sharon X Wen
(74) *Attorney, Agent, or Firm* — Parker Highlander PLLC

(57) ABSTRACT

In subjects with hypertension, increases in intima-media thickness (IMT) at four years were less in subjects also having high autoantibodies particularly IgM, to phosphorylcholine. The presence or absence of autoantibodies, particularly IgM, against phosphrylcholine is thus related to an increased or decreased risk of developing ischemic cardiovascular diseases. A method to determining antibodies, particularly IgM antibodies, toward phosphorylcholine is proposed in this invention to identify subjects at risk of developing ischemic cardiovascular diseases. Animal experiments show that medium to high levels of antibodies, particularly IgM antibodies, can be detected in plasma after active immunization with a keyhole limpet hemocyanin (KLH)-phosphorylcholine conjugate. Pharmaceutical compositions comprising a phosphorylcholine conjugate or antibody preparations, for example a monoclonal antibody, with specificity to a phosphorylcholine conjugate is proposed as is use of these compositions as active or passive immunogens in the treatment or prevention of atherosclerosis.

20 Claims, 8 Drawing Sheets

(56) References Cited

FOREIGN PATENT DOCUMENTS

Figure 1A:
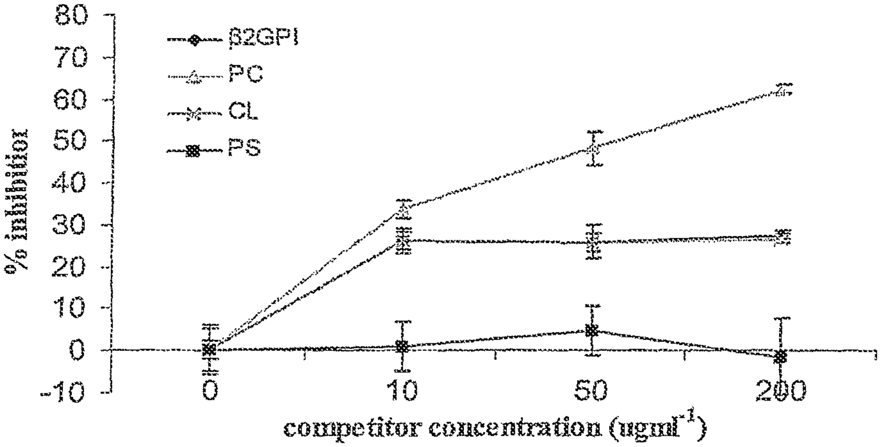

| | | |
|---|---|---|
| WO | WO 0188547 | 11/2001 |
| WO | WO 02/080954 | 10/2002 |
| WO | WO 04/091520 | 10/2004 |
| WO | WO 04/106486 | 12/2004 |

OTHER PUBLICATIONS

"Human Disease State Material and Clinical Samples: Rare Human Plasma," Product information from Sera Lab, available at http://www.seralab.co.uk/index.php?option=com_virtuemart&page=shop.browse&category_id=208&Itemid=42 , 2009.

Bergmark et al., "Patients with early-onset peripheral vascular disease have increased levels of autoantibodies against oxidized LDL," *Arterioscler Thromb Vasc Biol.*, 15:441-445, 1995.

Berliner et al., "Minimally modified low density lipoprotein stimulates monocyte endothelial interactions," *J. Clin Invest.*, 85:1260-1266, 1990.

Binder et al., "Innate and acquired immunity in atherogenesis," *Nature Medicine*, 8(11):1218-1226, 2002.

Binder et al., "Molecular Mimicry between Epitopes of Oxidized LDL and *Streptococcus pneumoniae*," *Abstracts from American Heart Association Scientific Sessions*, 2005.

Binder et al., "Pneumococcal vaccination decreases atherosclerotic lesion formation: molecular mimicry between *Streptococcus pneumoniae* and oxidized LDL," *Nature Medicine*, 9(6):736-743, 2003.

Binder, "Defining innate and adaptive immune mechanisms in the atheroprotective effect of immunization with oxidized low-density lipoproteins," *Dissertation Abstracts International*, 63(9):4109, 2005.

Bochkov et al., "Protective role of phospholipid oxidation products in endotoxin-induced tissue damage," *Nature*, 419:77-81, 2002.

Briles et al., "Anti-phosphorylcholine antibodies of the T15 idiotype are optimally protective against *Streptococcus pneumoniae*," *J. Exp Med.*, 156:1177-1185, 1982.

Chesebro and Metzger, "Affinity labeling of a phosphorylcholine binding mouse myeloma protein," *Biochemistry*, 11:7 66-771, 1972.

Chyu et al., "Changes in innate and adaptive humoral immune responses and indices of atherosclerosis in aging," *53rd Annual Scientific Session of the American College of Cardiology*, 2004.

Declaration from Hans Henriksnas, in the matter of European patent application No. 05735991.1, dated Jan. 4, 2010.

Declaration from Jan Brundell, in the matter of European patent application No. 05735991.1, dated Jan. 4, 2001.

Fei et al., "Oxidised LDL modulates immune-activation by an IL-12 dependent mechanism," *Atherosclerosis*, 169:77-85, 2003.

Frasch & Concepcion, "Specificity of human antibodies reactive with pneumococcal C polysaccharide," *Infection and Immunity*, 68:2333-2337, 2000.

Frostegård et al., "Biologically modified LDL increases the adhesive properties of endothelial cells," *Atherosclerosis*, 90:119-126, 1991.

Frostegård et al., "Cytokine expression in advanced human atherosclerotic plaques: dominance of pro-inflammatory (Th1) and macrophage-stimulating cytokines," *Atherosclerosis*, 145:33-43, 1999.

Frostegård et al., "Induction of T-cell activation by oxidized low density lipoprotein," *Arterioscler Thromb.*, 12:461-467, 1992.

Frostegård et al., "Oxidized low density lipoprotein induces differentiation and adhesion of human monocytes and the monocytic cell line U937," *Proc. Natl. Acad. Sci. USA*, 87:904-908, 1990.

Frostegård et al., "Platelet-activating factor and oxidized LDL induce immune activation by a common mechanism," *Arterioscler Thromb Vasc Biol.*, 17:963-968, 1997.

Frostegård, "Autoimmunity, oxidized LDL and cardiovascular disease," *Autoimmunity Reviews*, 1:233-237, 2002.

Gearhart et al., "Heterogeneity of the BALB/c antiphosphorylcholine antibody response at the precursor cell level," *Journal of Experimental Medicine*, 141(1):56-71, 1975.

Harnett and Harnett, "Immunomodulation by filarial nematode phosphorylcholine-containing glycoproteins," In: *Parasitic Nematodes*, CABI Publishing, Wallingford, UK, 399-414, 2001.

Harnett and Harnett, "Phosphorylcholine: friend or foe of the immune system," *Immunol. Today*, 20:125-129, 1999.

Heery et al., "Oxidatively modified LDL contains phospholipids with platelet-activating factor-like activity and stimulates the growth of smooth muscle cells," *J. Clin. Invest.*, 96:2322-2330, 1995.

Hulthe et al., "Antibodies to oxidized LDL in relation to carotid atherosclerosis, cell adhesion molecules, and phospholipase $A_2$," *Arterioscler Thromb Vasc Biol.*, 21:269-274, 2001.

Kameyama et al., "Convenient plasmid vectors for construction of chimeric mouse/human antibodies," *FEBS Letters*, 244(2):301-306, 1989.

Karvonen et al., "Immunoglobulin M type of autoantibodies to oxidized low-density lipoprotein has an inverse relation to carotid artery atherosclerosis," *Circulation*, 108:2107-2112, 2003.

Kearney, "Immune recognition of OxLDL in atherosclerosis," *Journal of Clinical Investigation*, 105(12):1683-1685, 2000.

Kim et al., "I-PLA2 activation during apoptosis promotes the exposure of membrance lysophosphatidylcholine leading to binding by natural immunoglobulin M antibodies and complement activation," *J. Exp. Med.*, 196(5):655-665, 2002.

Kitagawa et al., "Involvement of ICAM-1 in the progression of atherosclerosis in APOE-knockout mice," *Atherosclerosis*, 160(2):305-10, 2002.

Knoflach et al., "Immunity to heat shock proteins and atherosclerosis," In: *Heat Shock Proteins and Inflammation*, Birkhaeuser Verlag, Basel, Switzerland, 159-173, 2003.

Lim et al., "One-step 2-minute test to detect typhoid-specific antibodies based on particle separation in tubes," *Journal of Clinical Microbiology*, 36(8):2271-2278, 1998.

Malmö Diet and Cancer Study, available online at http://www.biobanks.se/malmodiet.htm, accessed Dec. 11, 2008.

Malmö Diet Cancer, 2008.

Office Communication issued in U.S. Appl. No. 10/599,934, dated May 12, 2009.

Office Communication issued in U.S. Appl. No. 10/599,934, dated Jul. 20, 2010.

Office Communication issued in U.S. Appl. No. 10/599,934, dated Jan. 20, 2011.

Padilla et al., "Levels of natural IgM antibodies against phosphorylcholine in healthy individuals and in patients undergoing isolated limb perfusion," *Journal of Immunological Methods*, 293:1-11, 2004.

Palinski et al., "Immunization of low density lipoprotein (LDL) receptor-deficient rabbits with homologous malondialdehyde-modified LDL reduces atherogenesis," *Proc. Natl. Acad. Sci. USA*, 92:821-825, 1995.

PCT International Search Report, dated Feb. 24, 2006.

Pockley et al., "Serum heat shock protein 70 levels predict the development of atherosclerosis in subjects with established hypertension," *Hypertension*, 42:235-238, 2003.

Purkall et al., "Opsonization of *Actinobacillus actinomycetemcomitans* by immunoglobulin G antibody reactive with phosphorylcholine," *Infection and Immunity*, 70(11):6485-6488, 2002.

Rose and Afanasyeva, "Autoimmunity busting the atherosclerotic plaque," *Nature medicine*, 9(6):641-642, 2003.

Salonen et al., "Autoantibody against oxidised LDL and progression of carotid atherosclerosis," *The Lancet*, 339(8798):883-887, 1992.

Schenkein et al., "Antiphosphorylcholine antibody levels are elevated in humans with periodontal diseases," *Infection and Immunity*, 67(9):4814-4818, 1999.

Schenkein et al., "Phosphorylcholine-dependent cross-reactivity between dental plaque bacteria and oxidized low-density lipoproteins," *Infection and Immunity*, 69(11):6612-6617, 2001.

Shaw et al., "Natural antibodies with the T15 idiotype may act in atherosclerosis, apoptotic clearance, and protective immunity," *The Journal of Clinical Investigation*, 105(12):1731-1740, 2000.

Shaw et al., "The autoreactivity of anti-phosphorylcholine antibodies for atherosclerosis-associated neo-antigens and apoptotic cells," *The Journal of Immunology*, 170(12):6151-6157, 2003.

Shoji et al., "Inverse relationship between circulating oxidized low density lipoprotein (oxLDL) and anti-oxLDL antibody levels in healthy subjects," *Atherosclerosis*, 148(1):171-177, 2000.

(56) References Cited

OTHER PUBLICATIONS

Simpson and Beachey, "Adherence of group A *Streptococci* to fibronectin on oral epithelial cells," *Infection and Immunity*, 39(1):275-279, 1983.
Spira et al., "T15 PC binding monoclonal antibodies retain specificity when they switch from IgM to IgG," *Journal of Immunology*, 140(8):2675-2680, 1988.
Stemme et al., "T lymphocytes from human atherosclerotic plaques recognize oxidized low density lipoprotein," *Proc. Natl. Acad. Sci. USA*, 92:3893-3897, 1995.
Subbanagounder et al., "Evidence that phospholipid oxidation products and/or platelet-activating factor play an important role in early atherogenesis: in vitro and in vivo inhibition by WEB 2086," *Circa Res.*, 85:311-318, 1999.
Svenungsson et al., "Risk factors for cardiovascular disease in systemic lupus erythematosus," *Circulation*, 104:1887-1893, 2001.
Takeoka et al., "Function of fibrinogen gamma-chain dodecapeptide-conjugated latex beads under flow," *Biochem. Biophys. Res. Commun.*, 312(3):773-779, 2003.
Todd et al., "Immunologic memory to phosphorylcholine VI. Heterogeneity in light chain gene expression," *European Journal of Immunology*, 15(2):177-183, 1985.
Trolle et al., "Intranasal immunization with protein-linked phosphorylcholine protects mise against a lethal intranasal challenge with *Streptococcus pneumoniae*," *Vaccine*, 18(26):2991-2998, 2000.
Wu et al., "Autoantibodies to OxLDL are decreased in individuals with borderline hypertension," *Hypertension*, 33:53-59, 1999.
Xu et al., "Induction of Arteriosclerosis in normocholesterolemic rabbits by immunization with heat shock protein 65," *Arterioscler. Thromb.*, 12:789-799, 1992.
Zanchetti et al., "Calcium antagonist lacidipine slows down progression of asymptomatic carotid atherosclerosis: principal results of the European Lacidipine Study on Atherosclerosis (ELSA), a randomized, double-blind, long-term trial," *Circulation*, 106:2422-2427, 2002.
Zanchetti et al., "Risk factors associated with alterations in carotid intima-media thickness in hypertension: baseline data from the European Lacidipine Study on Atherosclerosis," *J. Hypertension*, 16:949-961, 1998.
Hansson, "Inflammation, atherosclerosis, and coronary artery disease," *The New England Journal of Medicine*, 352(16):1685-1695, 2005.
Kita et al., "Role of oxidized LDL in atherosclerosis," *Annals New York Academy of Sciences*, 947:199-205. Discussion 205-206, 2001.
Lawson and Wolf, "ICAM-1 signaling in endothelial cells," *Pharmacological Reports*, 61:22-32, 2009.
Byers and Friedman, "Effect of infusions of phosphatides upon the atherosclerotic aorta in situ and as an ocular aortic implant", *J Lipid Res*, 1(4):343-8, 1960.
"Announcement of topline results from the GLACIER study", *Press Release*—BioInvent International AB, dated Jul. 11, 2012.
Abbas et al., "Chapter Three: Antibodies and Antigens", *Cellular and Molecular Immunolgoy*, 2$^{nd}$ Ed., p. 47, 1994. Print.
La Belle and Krauss, "Differences in carbohydrate content of low density lipoproteins associated with low density lipoprotein subclass patterns", *Journal of Lipid Research*, 31:1577-1588, 1990.
Morrison et al., "Chimeric human antibody molecules: mouse antigen-binding domains with human constant region domains", *Proc. Natl. Acad. Sci.*, 81:6851-6855, 1984.
Pearsall, Judy, ed. "Monoclonal Antibody", *The New Oxford Dictionary of English*, p. 1195, 2001.
Pettersson et al. "A fully human monoclonal IgG phosphorylcholine antibody prevents accelerated atherosclerosis in mice" (Poster) , American Heart Association Meeting, 2011.
Spira et al., "T15 PC binding monoclonal antibodies retain specificity when they switch from IgM to IgG", *The Journal of Immunology*, 140(8):2675-2680, 1988.
Technical Affidavit submitted in corresponding Indian Application No. 6634/DELNP/2006, dated Oct. 11, 2013.
Albers, Antithrombotic Therapy for Prevention and Treatment of Ischemic Stroke, Journal of Thrombosis and Thrombolysis 12(1), 19-22, 2001.
Cooke, The pathophysiology of peripheral arterial disease: rational targets for drug intervention, Vascular Medicine 1997: 2: 227-230.
Crouse et al., Clinical Manifestation of Atherosclerotic Peripheral Arterial Disease and the Role of Cilostazol in Treatment of Intermittent Claudication, J Clin Pharmacol 2002;42:1291-1298.
Dawson et al., Peripheral Arterial Disease: Medical Care and Prevention of Complications, Prev Cardiol. 2002 Summer;5(3):119-30.
Emsley and Tyrrell, Inflammation and Infection in Clinical Stroke, Journal of Cerebral Blood Flow & Metabolism 22:1399-1419, 2002.
Humphries and Morgan, Genetic risk factors for stroke and carotid atherosclerosis: insights into pathophysiology from candidate gene approaches, Lancet Neurol 2004; 3: 227-36.
Tegos et al., The Genesis of Atherosclerosis and Risk Factors: A Review, Angiology 52:89-98, 2001.
Casset, Florence, et al. "A peptide mimetic of an anti-CD4 monoclonal antibody by rational design." *Biochemical and Biophysical Research Communications* 307.1 (2003): 198-205.
Chang et al., "Monoclonal antibodies against oxidized low-density lipoprotein bind to apoptotic cells and inhibit their phagocytosis by elicited macrophages: evidence that oxidation-specific epitopes mediate macrophage recognition", *Proceedings of the National Academy of Science*, 96:6353-6358, 1999.
Chen, Yvonne, et al. "Selection and analysis of an optimized anti-VEGF antibody: mystal structure of an affinity-matured Fab in complex with antigen." *Journal of molecular biology* 293.4 (1999): 865-881.
De Pascalis, Roberto, et al. "Grafting of "abbreviated" complementarity-determining regions containing specificity-determining residues essential for ligand contact to engineer a less immunogenic humanized monoclonal antibody." *The Journal of Immunology* 169.6 (2002): 3076-3084.
Gearhart, Patricia J., et al. "IgG antibodies to phosphorylcholine exhibit more diversity than their IgM counterparts." Nature 291. 5810 (1981): 29-34.
Genbank, Accession No. J00253.1, Dated May 4, 2000, www.ncbi.nlm.nih.gov.
Hoet et al., "Generation of high-affinity human antibodies by combining donor-derived and synthetic complementarity-determining-region diversity", *Nature Biotechnology*, 23(3): 344-348, 2005.
Hörkkö et al., "Monoclonal autoantibodies specific for oxidized phospholipids or oxidized phospholipid-protein adducts inhibit macrophage uptake of oxidized low-density lipoproteins", *J Clin Invest*, 103(1):117-128, 1999.
Lamminmäki, Urpo, and Jussi A. Kankare. "Crystal structure of a recombinant anti-estradiol Fab fragment in complex with 17β-estradiol." *Journal of Biological Chemistry* 276.39 (2001): 36687-36694.
Libby, Peter, et al. "Macrophages and atherosclerotic plaque stability." Current opinion in lipidology 7.5 (1996): 330-335.
MacCallum, Robert M., Andrew CR Martin, and Janet M. Thornton. "Antibody-antigen interactions: contact analysis and binding site topography." *Journal of molecular biology* 262.5 (1996): 732-745.
Padlan, Eduardo A., et al. "Structure of an antibody-antigen complex: crystal structure of the HyHEL-10 Fab-lysozyme complex." *Proceedings of the National Academy of Sciences* 86.15 (1989): 5938-5942.
Palinski et al., "Cloning of monoclonal autoantibodies to epitopes of oxidized lipoproteins from apolipoprotein e-deficient mice", *J Clin Invest*, 98(3):800-814, 1996.
Plückthun et al., "Comparison of the Fv fragments of different phosphorylcholine binding antibodies expressed in *Escherichia coli*", *Annals of the New York Academy of Sciences*, 646:115-124, 1991.
Reape, Theresa J., and Pieter HE Groot. "Chemokines and atherosclerosis." Atherosclerosis 147.2 (1999):213-225.
Rudikoff, Stuart, et al. "Single amino acid substitution altering antigen-binding specificity." *Proceedings of the National Academy of Sciences* 79.6 (1982): 1979-1983.

(56) References Cited

OTHER PUBLICATIONS

Segal, David M., et al. "The three-dimensional structure of a phosphorylcholine-binding mouse immunoglobulin Fab and the nature of the antigen binding site." *Proceedings of the National Academy of Sciences* 71.11 (1974): 4298-4302.

Shaw et al., "Human-derived anti-oxidized LDL autoantibody blocks uptake of oxidized LDL by macrophages and localizes to atherosclerotic lesions in vivo", *Arterioscler Thromb Vasc Biol*, 21:1333-1339, 2001.

Vajdos, Felix F., et al. "Comprehensive functional maps of the antigen-binding site of an anti-ErbB2 antibody obtained with shotgun scanning mutagenesis." *Journal of molecular biology* 320.2 (2002): 415-428.

Wu, Herren, et al. "Humanization of a murine monoclonal antibody by simultaneous optimization of framework and CDR residues." *Journal of Molecular Biology* 294.1 (1999): 151-162.

| Key | Name | Parameter | Gate |
|---|---|---|---|
| —— | paf 1.004 | FL2-H | No Gate |
| (shaded) | CM.002 | FL2-H | No Gate |
| .... | P1-PC IgM.015 | FL2-H | No Gate |

PHOSPHORYLCHOLINE CONJUGATES AND CORRESPONDING ANTIBODIES

This application is a divisional of U.S. application Ser. No. 13/208,138, filed Aug. 11, 2011, which is a divisional of U.S. application Ser. No. 10/599,934, now U.S. Pat. No. 8,012,483, filed May 31, 2007, as a national phase application under 35 U.S.C. § 371 of International Patent Application No. PCT/GB2005/001463 filed Apr. 15, 2005, which claims priority to U.S. Provisional Patent Application No. 60/521,384 filed Apr. 15, 2004. The entire texts of the above-referenced disclosures are specifically incorporated herein by reference without disclaimer.

FIELD OF THE INVENTION

This invention relates to the field of treatment and risk assessment for atherosclerosis and ischemic cardiovascular diseases.

DESCRIPTION OF RELATED ART

Atherosclerosis is a chronic disease that causes a thickening of the innermost layer (the intima) of large and medium-sized arteries. It decreases blood flow and may cause ischemia and tissue destruction in organs supplied by the affected vessel. Atherosclerosis is the major cause of cardiovascular disease including myocardial infarction, stroke and peripheral artery disease. It is the major cause of death in the western world and is predicted to become the leading cause of death in the entire world within two decades.

The disease is initiated by accumulation of lipoproteins, primarily low-density lipoprotein (LDL), in the extracellular matrix of the vessel. These LDL particles aggregate and undergo oxidative modification. Oxidized LDL is pro-inflammatory, toxic and causes vascular injury. Atherosclerosis represents in many respects a response to this injury including inflammation and fibrosis.

In 1989 Palinski and coworkers identified circulating autoantibodies against oxidized LDL in humans. This observation suggested that atherosclerosis may be an autoimmune disease caused by immune reactions against oxidized lipoproteins. At this time several laboratories began searching for associations between antibody titers against oxidized LDL and cardiovascular disease. However, the picture that emerged from these studies was far from clear. Antibodies existed against a large number of different epitopes in oxidized LDL, but the structure of these epitopes was unknown. The term "oxidized LDL antibodies" thus referred to an unknown to mixture of different antibodies rather than to one specific antibody.

It is well established that there is an ongoing inflammation in the atherosclerotic lesions, characterized by activation of immune competent cells and production of inflammatory cytokines. Established risk factors like hypertension, blood lipids, diabetes and smoking are likely to promote this inflammatory reaction, but the mechanism by which this occurs are not well characterized and different non-mutually exclusive possibilities exist. Several different autoantigens that could elicit this immune reactivity have been proposed, including oxidized low density lipoprotein (oxLDL) and heat shock proteins (HSP)[2,3]. Available data on the role of immune reactions in atherosclerosis indicate a complex relationship. One example of this is immunization in animal models to influence atherogenesis. When HSP is used, atherosclerosis increases but decreases when oxLDL is the antigen[4,5].

The role of aOxLDL in human disease appears to be complex. In humans, it has previously been demonstrated that aOxLDL is higher in healthy controls than in men with borderline hypertension, an example of early cardiovascular disease[6]. Recent studies are in line with this observation[7,8]. On the other hand, several authors have reported that aOxLDL are raised in human cardiovascular diseases (CVD), especially at later stages[2,3,9,10]. One example is systemic lupus erythematosus (SLE) and autoimmune disease associated with a very high risk of CVD. SLE-patients with a history of CVD had clearly raised aOxLDL-levels[11]. These to some extent contradictory results may depend on different methods and stages of LDL-oxidation, yielding differences in antigenicity. It is also likely that disease stage and risk factor profile are related to antibody levels.

Oxidized low density lipoprotein (oxLDL) itself has many proinflammatory properties including activation of T cells[12,13], monocytes/macrophages and endothelial cells[14-16]. OxLDL promotes inflammation also in immune competent cells from atherosclerotic lesions[17]. However, it should be noted that oxLDL may also ameliorate acute inflammatory reactions and instead promote a more low-grade chronic inflammation as that seen in atherosclerosis[18]. It is interesting to note that many biological effects of oxLDL are caused by platelet activating factor (PAF)-like lipids in oxLDL[19-21].

Phosphorylcholine (PC) is a major component not only in inflammatory phospholipids like platelet activating factor-PAF (where it is essential for interaction with the PAF-receptor) and in oxLDL, but is also as an immunogenic components of many bacteria including *S. Pneumoniae*[22]. Furthermore, PC is expressed by apoptotic cells[2,23].

In U.S. Pat. No. 5,455,032 phosphocholine conjugates have been used in vaccines for inducing immunoprotection against infections such as *Streptococcus pneumoniae*. In a recent study[24] by Binder et al on pneumococcus vaccine in mice, it was also shown that vaccination decreased atherosclerotic lesion formation. It was found that many autoantibodies to oxLDL derived from atherosclerotic mice share structural identity with antibodies which protect against common infectious pathogens, including *Streptococcus pneumoniae*. The study, in mice, not humans, does not give any information about specificity, or that IgM anti-phosphorylcholine antibodies are significantly more important than corresponding IgG antibodies as a protecting factor in atherosclerosis. Furthermore, phosphorylcholine conjugates have not been used in the pneumococcus vaccine.

In another study it was shown[25] that antiphosphorylcholine antibody levels are elevated in humans with periodontal diseases. The conclusion is that phosphorylcholine is an important oral antigen associated with organisms in the periodontal flora and that anti-PC antibody is elevated as a consequence of periodontal disease. No information is given with regards to the antibodies and possible protection from or progression of atherosclerosis.

A couple of documents (e.g. WO2002080954 and WO0168119) related to immunization treatment of atherosclerosis have been published but these are either based on the use of peptide fragments of apolipoprotein B or antibodies to alpha/beta chains of a T cell receptor. A method to detect atherosclerotic plaque (WO9908109) using monoclonal antibodies to oxidation-specific epitopes on lipoprotein has also been described. This is different from the method proposed in this invention where a phosphorylcholine conjugate is used to detect antibodies, eg IgM or IgG antibodies, in subject samples.

SUMMARY OF THE INVENTION

The invention relates to pharmaceutical compositions comprising a phosphorylcholine conjugate, or an antibody preparation, for example a monoclonal antibody, with specificity to a phosphorylcholine conjugate, and the use of these compositions in the treatment or prevention of atherosclerosis, for example in the treatment, prevention or reduction of further progression of atherosclerosis Furthermore, the invention also relates to the use of phosphorylcholine conjugates or said antibody preparation, for example monoclonal antibody to produce a pharmaceutical composition optionally with an adjuvant. Furthermore the invention relates to diagnosing the presence or absence of antibodies, for example IgM or IgG antibodies, related to increased or decreased risk of developing ischemic cardiovascular diseases.

A first aspect of the invention provides the use of a pharmaceutical composition comprising at least one phosphorylcholine conjugate, or an antibody preparation, for example a monoclonal antibody, with specificity to a phosphorylcholine conjugate, in the manufacture of a medicament for immunization and treatment of mammals, including humans, against atherosclerosis or an atherosclerotic related disease. The medicament is intended to provide immunization having immunogenic or therapeutic properties against atherosclerosis.

A second aspect of the invention provides a method for immunization and treatment of a mammal, including a human, against atherosclerosis or an atherosclerotic related disease, the method comprising the step of administering to the mammal a pharmaceutical composition comprising at least one phosphorylcholine conjugate, or an antibody preparation, for example a monoclonal antibody, with specificity to a phosphorylcholine conjugate. The pharmaceutical composition is intended to provide immunization having immunogenic or therapeutic properties against atherosclerosis.

By phosphorylcholine conjugate is meant a phosphorylcholine moiety linked to a carrier, preferably via a spacer. The structural element phosphorylcholine may comprise a derivative of phosphorylcholine. Examples of suitable phosphorylcholine conjugates are described in U.S. Pat. No. 5,455,032, as noted above. For example, U.S. Pat. No. 5,455,032 provides phosphorylcholine conjugates in which the phosphorylcholine moiety is linked by a straight chain alkyl and an amide linkage to a variety of immunological carriers. The phosphorylcholine conjugate may for example be a human serum albumin (HSA)- or keyhole limpet hemocyanin (KLH)-phosphorylcholine conjugate or a bovine serum albumin (BSA)-phosphorylcholine conjugate (for example as described in the Examples). PC-BSA (Phosphorylcholine-Bovine Serum Albumin) can be purchased from Biosearch Technologies, INC(Ca, USA). HSA-BSA-can be conjugated by a chemical procedure, for example the following procedure:

O-(4-aminophenyl phosphoryl)-choline (I) can be prepared from O-(4-nitrophenyl-phosphoryl)-choline (Sigma N 5879) in quantitative yield by reduction with hydrogen gas at 1 atm with 10% palladium at charcoal as a catalyst, according to a procedure described by Chesebro, B. in Biochemistry 11, (1972) 766.

(I) can be coupled to HSA by means of EDC (1-ethyl-3-(3-dimethyl-aminopropyl)-carbodiimide) in MES buffer pH 4, essentially according to a procedure described by Padilla, N. D. et al in J. Immun. Methods 293 (2004) 1-11. The conjugated HSA can isolated by dialysis against buffered saline at pH 7.4.

The carrier can be, for example, a protein, lipid or polymer. The carrier can be latex beads, for example as described in the Examples.

The medicament may be intended for administration by injection.

A further aspect of the invention provides the use of one or more of the phosphorylcholine conjugates as defined in relation to the preceding aspects of the invention, in the manufacture of a pharmaceutical composition, optionally in combination with an adjuvant, for immunotherapy or therapy for the treatment of ischemic cardiovascular diseases.

A further aspect of the invention provides a method of prophylactic or therapeutic treatment of a mammal, which may be a human being, suffering from atherosclerosis or facing the risk of developing ischemic cardiovascular disease, whereby a therapeutically effective amount of at least one phosphorylcholine conjugate or an antibody preparation, for example a monoclonal antibody, with specificity to a phosphorylcholine conjugate is administered.

The invention also relates to methods to determine the presence or absence of antibodies, for example IgM or IgG antibodies, against phosphorylcholine which are related to an increased or decreased risk of developing ischemic cardiovascular diseases.

A further aspect of the invention provides a method of diagnosing the presence or absence of antibodies, for example IgM or IgG antibodies, related to increased or decreased risk of developing ischemic cardiovascular diseases, using a phosphorylcholine conjugate.

Thus, a further aspect of the invention provides the use of a phosphorylcholine conjugate in a method for assessing a patient's risk of developing or progression of ischemic cardiovascular disease in which the patient's levels of antibodies, for example IgM or IgG antibodies, reactive with the phosphorylcholine conjugate are assessed.

Phosphorylcholine conjugates are described above. The phosphorylcholine may be linked to a carrier via a spacer. The carrier may be a protein, which may be KLH (keyhole limpet hemocyanin) or human serum albumin (HSA). The carrier may be latex beads.

The patient's levels of antibodies, eg IgM or IgG antibodies, reactive with the phosphorylcholine conjugate may be assessed using an immunoassay. Examples of suitable immunoassays are described below and will in any case be apparent to those skilled in the art.

It may be desirable to measure antibodies reactive with oxLDL or MD-LDL as well as measuring antibodies, eg IgM or IgG antibodies, reactive with the phosphorylcholine conjugate. It may alternatively or in addition be desirable to measure levels of HSP70, HDL, TNF and/or HSP60 (as discussed in the Examples) as well as measuring antibodies, eg IgM or IgG antibodies, reactive with the phosphorylcholine conjugate.

DETAILED DESCRIPTION OF THE INVENTION

The examples disclosed below are provided only for the purpose of illustrating the present invention and should not be considered as any limitation of the scope as outlined in the appended claims. Document referred to herein are hereby incorporated by reference.

An example of a method to determine the presence or absence (or level) of IgM antibodies against phosphorylcholine which is related to an increased or decreased risk of developing ischemic cardiovascular diseases is described. Other methods known in the art can also be used. Similar methods may be used to determine the presence or absence (or level) of IgG antibodies against phosphorylcholine.

Methods to Determine the Presence or Absence of IgM Antibodies Against Phosphorylcholine IgM antibodies to PC-BSA were determined by an enzyme-linked immunosorbent assay method.

A microtiter plate was coated with PC-BSA (10 μg/ml; for example from Biosearch Technologies, INC (Ca, USA) in phosphate buffered saline (PBS). After washings with PBS, the plates were blocked with a 2% BSA solution. Serum samples were diluted (1:30) in 0.2% BSA-PBS. Plates were incubated overnight at 40° C. and washed. Alkaline phosphatase conjugated goat anti-human IgM (diluted 1:7000 in the sample buffer) were added at 100 ul/well and incubated at 40° C. overnight. After washings, colour was developed by adding an alkaline phosphatase substrate and incubating the plates for 60 min at room temperature in the dark. The absorbances were read in a spectrophotometer at 405 nm.

Different carriers and spacers for phosphorylcholine have been tested. The exemplified carriers are not limited to these. Other carriers such as other proteins, lipids or polymers, such as latex beads which are known in the art, may also be used. Carriers are discussed in U.S. Pat. No. 5,455,032, as noted above.

The IgM or IgG antibodies detected by a method of the invention may also bind to phosphorylcholine (PC) present in PC-containing compounds in which PC is exposed, for example in lysophosphatidylcholine (lysoPC; see, for example, Kim et al, J Exp Med. 2002 Sep. 2; 196(5):655-65). Thus, a method of the invention may detect IgM or IgG antibodies that bind to lysphosphatidylcholine.

Synthesis of a Phosphorylcholine Conjugate and Preparation of a Pharmaceutical Composition Latex beads (0.20 μm or 0.81 μm) were suspended in PBS and mixed over night with a 10 μg/ml solution of phosphorylcholine-BSA. The beads were then centrifuged and washed several times with buffer and blocked with a 10 μg/ml solution of BSA. After another repeated washing, the beads were resuspended to a suitable concentration in a suitable buffer and stored refrigerated until use.

Phosphorylcholine with a linker arm can also be conjugated to KLH (keyhole limpet hemocyanin) via a diazophenyl group. More preferably a p-nitrophenyl-6-(O-phosphocholine)hydroxyhexanoate derivative of PC can be synthesized according to Chesebro, B. and Metzger, H. (1972) *Biochem.* 11:776. p-Nitrophenyl-6-(O-phosphocholine) hydroxyhexanoate was dissolved in dry acetonitrile (100 mg/ml) just prior to adding it to the KLH. Derivative and KLH were mixed overnight at 4° C. and then dialyzed to remove unbound spacer and p-nitrophenylate, which is the leaving group.

An injection solution of the prepared phosphorylcholine conjugate, suspended in a suitable buffer, can be directly used for immunization.

Immunization with a Phosphorylcholine Conjugate

A high titer of IgM antibodies recognizing phosphorylcholine was determined in plasma from BALB/c mice after immunization with 200 μg [p-Nitrophenyl-6-(O-phosphocholine) hydroxyhexanoate-KLH] i.p. using the suggested immunoassay method.

Monoclonal Antibodies Against a Phosphorylcholine Conjugate

Monoclonal antibodies can be produced using any standard method known in the art. See for example "Briles D E, Forman C, Hudak S, Claflin J L. Anti-phosphorylcholine antibodies of the T15 idiotype are optimally protective against *Streptococcus pneumoniae. J Exp Med.* 1982; 156: 1177-85" or "T15 PC binding monoclonal antibodies retain specificity when they switch from IgM to IgG., Spira, Gad; Aguila, Hector L.; Scharff, Matthew D. Fac. Med., Techniton-Israel Inst. Technol., Haifa, Israel. *Journal of Immunology* (1988), 140(8), 2675-80.

Other antibodies against a phosphorylcholine conjugate can be prepared using methods well known to those skilled in the art. For example, a subfraction with aPC activity of a human immunoglobulin preparation can be prepared, for example as described below, for example by affinity purification using a phosphorylcholine conjugate. Intravenous immunoglobulin preparations (e.g. IGIV; Baxter and others) is a highly purified preparation of IgG commercially available and is used in the treatment of patients who have no, or very low levels of antibody production. Immunoglobulin preparations include those available from the following manufacturers: Baxter (US) eg Gammagard®, Isiven (Antimo Naples, Italy), Omrix (Tel-Hashomer, Israel), Miles (Biological Products Division, West Heaven, Conn.), Sclavo (Lucca, Italy), Sandoz (Novartis, Basel, Swizerland) eg Sandoglobulin®, Biotest Diagnostic Corporation (Deville, N.J.). Examples of immunoglobulin preparations are Gammagard S/D®, Gammar IV®, Gammar-P IV®, Gammimune N®, Iveegam®, Panglobulin®, Polygam S/D®, Sandoglobulin®, Venoglobulin®. Immunoglobulin preparations typically contain some IgM as well as IgG. Trace amounts of IgM are present in Gammagard®. Pentaglobin (Biotest) is an enriched IgM preparation which has been used for treatment of SARS. The subfraction with aPC activity may comprise both IgG and IgM, or may be selected to comprise mainly IgG (for example by starting with an IgG-rich preparation such as Gammagard® and/or by selecting for IgG); or mainly IgM (for example by starting with an IgM-rich preparation such as Pentaglobin and/or by selecting for IgM).

An antibody preparation with specificity to a phosphorylcholine conjugate binds to unconjugated phosphorylcholine and may also bind to phosphorylcholine (PC) present in PC-containing compounds in which PC is exposed, for example in lysophosphatidylcholine (lysoPC; see, for example, Kim et al, J Exp Med. 2002 Sep. 2; 196(5):655-65). Thus, an antibody preparation with specificity to a phosphorylcholine conjugate may also bind to lysphosphatidylcholine.

IgM Immunoglobulin Levels in Atherosclerotic Subjects

IgM autoantibody levels against phosphorylcholine in subjects with hypertension (diastolic pressure>95 mmHg) were determined at baseline and after 4 years in a correlation study of risk factors for atherosclerosis. The results are summarized below.

Carotid plaques were detected in 77 subjects (35%) at enrolment, and in 84 subjects (38%) at the 4-year follow-up. In total 218 human subjects were in the study. Increases in intima-media thickness (IMT) at follow-up were less prevalent in subjects having high serum levels of IgM to PC ($75^{th}$ or $90^{th}$ percentile) at the time of enrolment. There is a significant difference between mean values in IgM anti-phosphorylcholine antibody levels between individuals with increased and decreased IMT (638.8±219.6 vs. 734.8±266.9, p=0.004).

The relationships between IgM autoantibodies to PC and changes in IMT were independent of age, smoking habits, treatment with atenolol or lacidipine and blood lipids. IgM autoantibodies were also independent of IgG values.

One embodiment of the present invention is thus to use a phosphorylcholine conjugate for the preparation of a pharmaceutical composition to be used in the treatment or prevention of atherosclerosis. The conjugate can be phosphorylcholine linked to a protein or to a polymer. The pharmaceutical composition is preferably given by injection.

The proposed method of active immunization will modulate the autoantibodies titer which in turn will have a positive effect on the development of atherosclerosis.

Another embodiment of the invention is to use an antibody preparation, for example a monoclonal antibody, recognizing a phosphorylcholine conjugate for the preparation of a pharmaceutical composition to be used in the treatment or prevention of atherosclerosis. The monoclonal antibody can be produced using methods known in the art.

A further embodiment of the invention is to provide a method of diagnosing the presence or absence of antibodies, for example IgM or IgG antibodies, towards phosphorylcholine which factor is related to an increased or decreased risk of developing ischemic cardiovascular diseases, using a phosphorylcholine conjugate. A preferred method is an immunoassay. The method may be used in assessing the patient's risk of developing or progression of ischemic cardiovascular disease.

FIGURES

FIG. 1*a*: Inhibition of antibody (IgM) binding to ELISA-plates coated with PC albumin by β2GPI, PS and CL. Inhibition by different antigens of binding to PC albumin-coated plates. In order to investigate the specificity of aPC, competition assays were performed as described in the Experimental section. Results are presented as mean±SD.

Figure 1B:
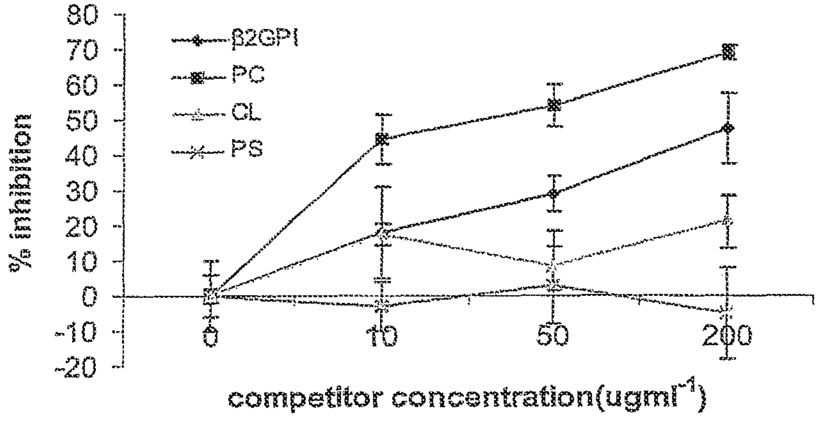

FIG. 1*b*: Inhibition of antibody (IgG) binding to ELISA-pates coated with PC albumin by β2GPI, PS and CL. Inhibition by different antigens of binding to PC albumin-coated plates. In order to investigate the specificity of aPC, competition assays were performed as described in the Experimental section. Results are presented as mean±SD.

Figure 2A:
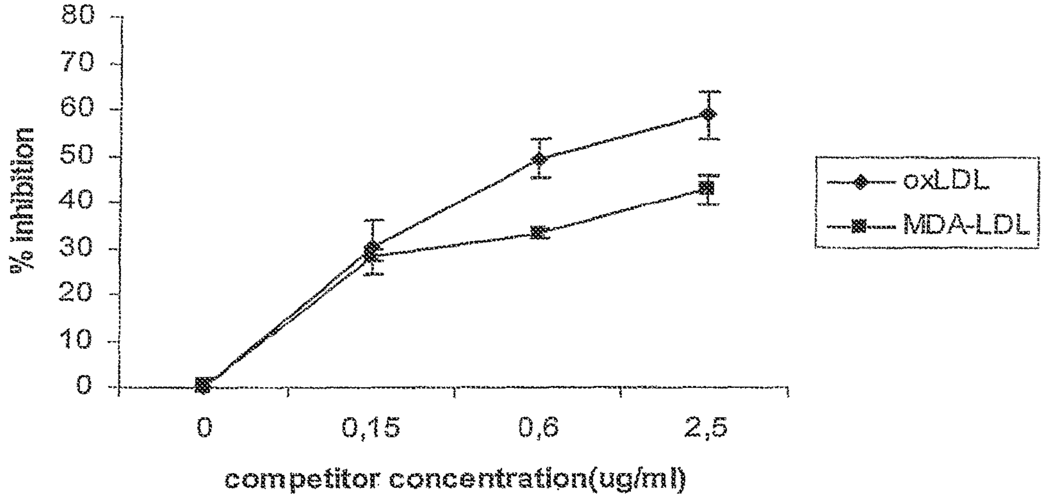

FIG. 2*a*: Inhibition of antibody (IgM) binding to ELISA-pates coated with PC albumin by oxLDL and MDA-LDL. Inhibition by different antigens of binding to PC albumin-coated plates. In order to investigate the specificity of aPC, competition assays were performed as described in the Experimental section. Results are presented as mean±SD.

Figure 2B:
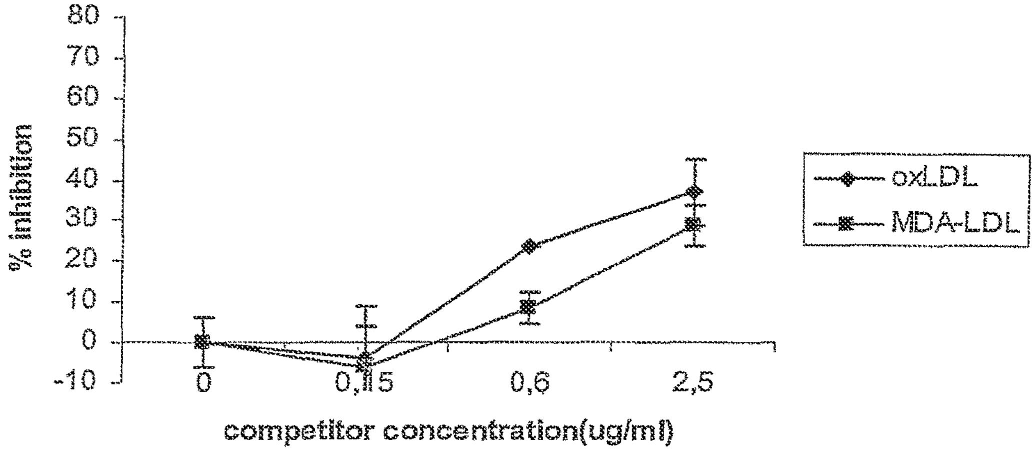

FIG. 2*b*: Inhibition of antibody (IgG) binding to ELISA-pates coated with PC albumin by oxLDL and MDA-LDL. Inhibition by different antigens of binding to PC albumin-coated plates. In order to investigate the specificity of aPC, competition assays were performed as described in the Experimental section. Results are presented as mean±SD.

Figure 3A:
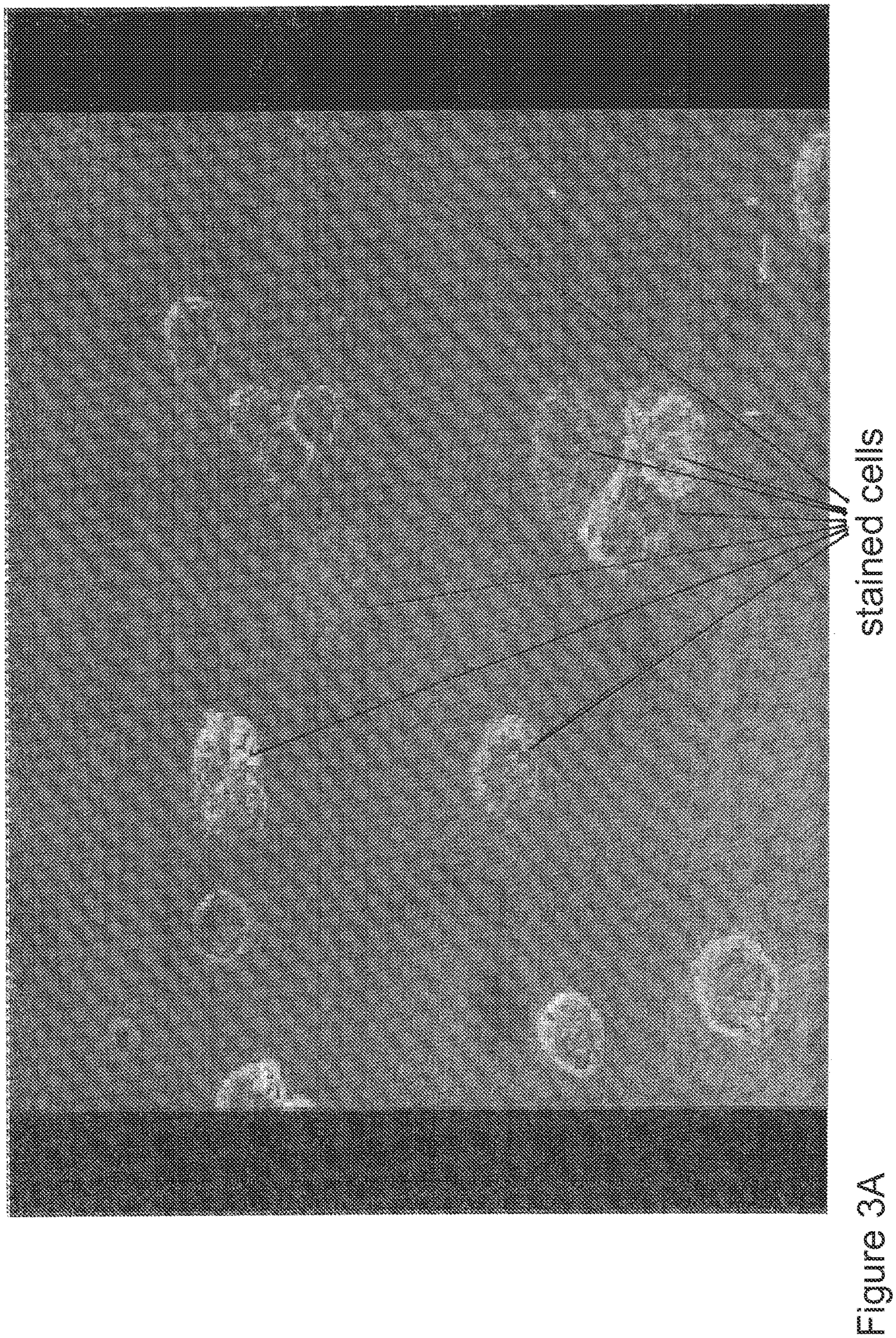
Figure 3B:

FIGS. 3*a*-3*b*: effect on oxLDL uptake in macrophages by aPC extracted from IGIV We tested two groups: macrophages with oxLDL and macrophages with oxLDL+preincubation with aPC extracted from IVIG.

macrophage+-oxLDL (total 107 cells):

Weak staining 37/107=34.58%

Strong Staining 10/107=9.35% total staining positive 47/107=43.93% macrophage+Dil-oxLDL+aPC-group (checked 156 cells):

Weak staining 37/156=23.72%

Strong Staining 2/156=1.28% total staining positive 39/156=25%.

FIG. 3A shows staining with Dil-labelled oxLDL. FIG. 3B shows staining with unlabeled oxLDL.

Figure 4:
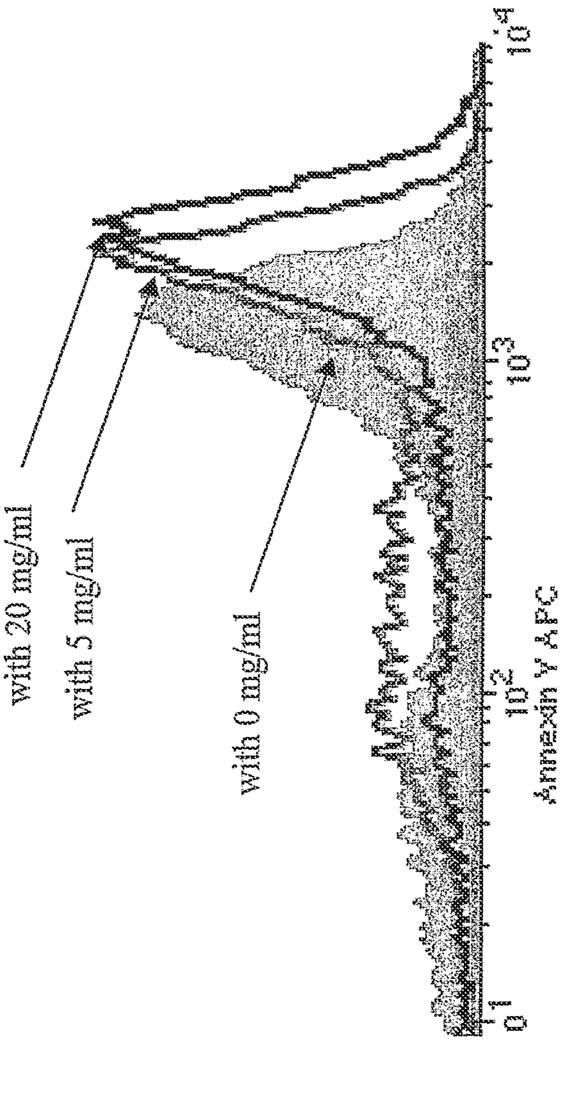

FIG. 4: Effect of pre-incubation of high antiphospholipid antibodies (aPLs) titer serum with human pooled immunoglobulin Gammagard® on Annexin V binding to human umbilical endothelia cells (HUVECs): flow cytometry analysis after 24 hrs culture.

| IVIG pre-incubated with serum at | Median fluorescence intensity (MFI) of Annexin V binding |
|---|---|
| 0 mg/ml | 649 |
| 2.5 mg/ml | 913 |
| 5 mg/ml | 1269 |
| 10 mg/ml | 1382 |

Figure 5:
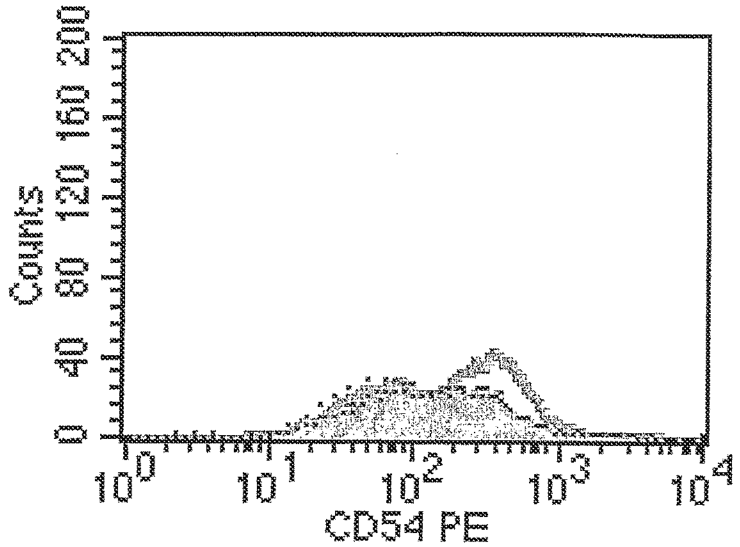

FIG. 5: effect of aPC on ICAM-induction in endothelial cells 1 ug/ml of PAF was added to cultures of endothelial cells, with or without preincubation with aPC IgM. Expression of ICAM-1 was tested by FACScan. Green line represents PAF effect, while red is PAF+aPC IgM and black control. The data clearly indicate a shift to the left of histogram when aPC IgM are added.

EXPERIMENTAL

Subjects

Serum samples were obtained from 226 subjects with established hypertension (diastolic pressure >95 mm Hg) prior to their entry into the Swedish component of the European Lacidipine Study on Atherosclerosis (ELSA)[25,26]. Samples were collected following a 4-week washout period with no medication to minimize the effects of treatment on the measured parameters. Blood pressure, cholesterol and triglyceride levels were determined as described previously[25,26]. One hundred and fifteen of the subjects were subsequently assigned to treatment with the β-blocker atenolol, and 111 of the subjects were assigned to treatment with the calcium antagonist lacidipine. The study was approved by the Ethics Committee of the Karolinska Hospital and was conducted in accordance with the Helsinki Declaration. All subjects gave informed consent.

Carotid Ultrasound

Carotid ultrasound determinations were performed and analysed as detailed elsewhere25,26. A total of 218 patients had valid ultrasound measurements at baseline and 4-year follow up. Briefly, the right and left carotid arteries were examined with Biosound 2000 IIA duplex scanner using an 8.0 MHz annular array transducer. The intima-media (I-M) thickness was determined in the far wall as the distance between the leading edge of the lumen-intima echo and the leading edge of the media-adventitious echo. The outcome measurement as a surrogate indicator for atherosclerosis was the change in mean maximum Intimal-Medial thickness (IMT) of the four far walls in the distal common carotids and carotid bifurcations bilaterally (CBMmax) at the 4-year follow-up. The associations between antibody levels to PC at enrolment into the study with an increase or decrease in IMT at the 4-year follow-up were evaluated.

Reagents

Polysorp F96 microtiter immuno-plates were purchased from Nunc (Roskilde Denmark), PC-BSA (Phosphorylcholine-Bovine Serum Albumin) was purchased from Biosearch Technologies, INC (USA).

Bovine serum albumin (BSA), Alkaline phosphatase conjugated goat anti-human IgG (r-chain specific), Alkaline phosphatase conjugated goat anti-human IgM (u-chain specific), PNPP (Alkaline phosphatase substrate), were obtained from Sigma (St. Louis, Mo., USA). Cardiolipin (CL) was purchased from AVANTT (US, $\beta_2$glycoprotein ($\beta_2$GP1) was obtained from Calbiochem (US).

Total IgG and IgM levels were determined by routine techniques as previously described[6].

CRP was analyzed in erum by highly sensitive methods using particle-enhanced immunonephelometry (Behring Nephelometer Analyzer, BN II (Dade Behring GmBH, Marburg, Germany)) with an antir-assay variation <4%.

Determination of Autoantibodies Against PC, oxLDL and MDA-LDL

IgG and IgM antibodies to PC-BSA were determined by enzyme-linked immunsorbent assay (ELISA). Pooled serum from 17 antiphospholipid syndrome patients was used as an internal standard and tested on every plate. The plateau of antibody binding was reached with the antigen concentration of 10 g/ml. F96 microtiter polysorp pate was therefore coated with PC-BSA (10 μg/ml) 50 μg·well in PBS. Coated plates were incubated overnight at 4° C. After five washings with PBS, the plates were blocked with 2% BSA-PBS for 2 h at room temperature and washed as described above. Serum saples were diluted (1:30) in 0.2% BSA-PBS and added at 50 μl/well.

LDL was isolated from plasma of healthy donors by sequential preparative ultra-centrifugation and oxidized by use of copper ions (OxLDL) or derivatized with MDA (MDA-LDL) as described[6].

OxLDL and MDA-LDL were determined by ELISA essentially as described[6]. OxLDL or MDA-LDL was diluted to 2 μg/ml in coating buffer (carbonate-bicarboatne buffer 50 mM pH9.7), and 100 μl/well was used to coat ELISA plates (Costar 2581). The plates were kept at 4° C. overnight, washed 4 times with PBS, and then blocked with 20% adult bovine serum in PBS (20% ABS-PBS) for 2 horus in room temperature. They were then incubated with 100 μl serum, diluted 1:30 in 20% ABS-PBS at 4° C. overnight.

Plates were incubated overnight at 4° C. and washed as described above. Alkaline phosphatase conjugated goat anti-human IgG (diluted 1:9000 in the sample buffer) and Alkaline phosphatase conjugated goat anti-human IgM (diluted 1:7000 in the sample buffer) were added at 1001/well and incubated at 4° C. overnight. After five washing, color was developed by adding the alkaline phosphatase substrate (PNPP) at 100 μl/well and incubating the plates for 60 min at room temperature in the dark. The plates were read in an ELISA Multiskan Plus spectrophotometer at 405 nm. All samples were measured in a single assay and the coefficient of variation was below 10-15%.

Specificity of Anti-Phosphorylcholine-BSA Antibodies

In order to investigate the specificity of anti-phosphorylcholine-BSA, absorption assays were performed by use of pooled high titer sera. At a dilution giving 50% of maximal binding to PC-BSA, high titer pooled sera were preincubated with different concentration of PC-BSA. After vortexing, the tubes were incubated at 40° C. overnight and centrifuged at 13000 r.p.m. for 30 min (40° C.) The supernatants were tested for antibody binding to PC-BSA as described. The percentage of inhibition was calculated as follows:

$$\text{Percent inhibition}=(OD\text{ without competitor}-OD\text{ with competitor})\times 100/OD\text{ without competitor.}$$

Statistical Analysis anti-phosphorylcholine levels were dichotomized at the 75th and 90th percentile. The association between anti-phosphorylcholine (or other antibodies) and the progression of atherosclerosis over a 4-year period were determined by estimating increases in IMT (yes or no) using logistic regression analysis and the calculation of odds ratios (ORs) and 95% confidence intervals (CI), or comparison using Spearman correlation as indicated. Adjustments were made for possible confounders including age, smoking habits, serum cholesterol, serum triglycerides and mode of anti-hypertensive treatment (lacidipine, atenolol). A two-tailed p-value <0.05 was considered as significant.

Results

Basic characteristics of the subjects at the time of enrolment into the study have been detailed elswhere (Pockley et al (2003) Hypertension 42, 235-238) and are presented in Table I.

Competition studies reveal that aPC of IgM and IgG subclass was competed out by preincubation with PC-BSA, while cardiolipin had a weak and phosphatidylserine no competitive capacity (FIG. 1*a*, 1*b*). β2-glycoprotein I competed to some extent with IgG binding to PC-BSA but not so much with IgM (FIG. 1*a*, 1*b*). PC-BSA had a low capacity to compete out binding to the other antigens tested (data not shown). OxLDL and MDA-LDL could compete out binding of IgM aPC to PC-BSA, and also of IGG aPC, though not to the same extent (FIG. 2*a*, 2*b*).

Increases in IMT at follow-up were less prevalent in subjects having high serum levels of IgM to PC (75th or 90th percentile), oxLDL and MDA-LDL (90th percentile) at the time of enrolment, while CRP was not associated with IMT-changes (Table 2).

Logistic regression analysis revealed that the relationships between IgM autoantibodies to PC, oxLDL and MDA-LDL and changes in IMT were independent of age, smoking habits, treatment with atenolol or lacidipine and blood lipids. aPC IgM were significantly associated with changes in IMT at both 75th and 90th percentile, while aOxLDL and aMDA-LDL of IgM subclass only showed significance at the 90th (table 3a-d). IgM autoantibodies were also independent of IgG values (data not shown). Furthermore, total IgG and IgM levels were not associated with IMT-measurements or changes (data not shown).

IgG autoantibodies to PC were trendwise lower in subjects with increases in IMT but this difference did not reach statistical significance (Table 2).

There were striking differences between men and women. aPC, aMDA-LDL, and aOxLDL of IgM subclass, were significantly higher in women than in men (p's<0.05). In contrast, there were no differences between men and women in IgG levels of these autoantibodies. In addition, women had a significantly lower occurrence of plaque at baseline and follow-up (p<0.05).

aPC IgM levels correlated negatively with increase in IMT (Rho 0.18, p=0.006) in contrast to two other protection factors, HDL and HSP70 which did not correlate with IMT changes as continuous measurements (data not shown). Unlike aPC IgM, aOXLDL and aMDA-LDL did not reach significance in these determinations (data not shown).

There were significant associations between aPC IgM levels and aOCLDL IgM (Rho 0.74, p<0.001) and aMDA-LDL IgM (rho 0.51, p<0.001). Likewise aPC correlated with HSP60 (Rho 0.28, p<0.001), HSP70 (Rho 0.35, p<0.001), which we recently described as a novel protective afactor for human athersclerosis in this cohort (Pockley et al (2003) supra) and also with HDL (Rho 0.23, p<0.01). There were not associations between aPC IgM, aOxLDL IgM or aOx-LDL, MDA-LDL and LDL, CRP or triglycerides (data not shown).

When separate logistic regression analyses were made for men and women, controlling for age, total cholesterol, triglycerides, smoking and treatment IgM aPC showed significant protective effects in women only when 90th percentile was studied (EXP (B)=0.17, 95% CI=0.05-0.68; p=0.01 and in men only when 75th percentile was studied EXP (B)=0.18, 95% CI=0.04-0.74; p=0.01, respectively).

IgM to MDA-LDL and oxLDL differend in this respect, since only values for women reached statistical significance independently. Thus, when separate logistic regression analyses were to made for men and women, controlling for age, total cholesterol, triglycerides, smoking and treatment both IgM to MDA-LDL and IgM to OxLDL showed significant protective effects in women (EXP (B)=0.17, 95% CI=0.05-0.68, p=0.01 and EXP (B)=0.18, 95% CI=0.04-0.74, p=0.01, respectively), whereas the effect did not reach significance among men (EXP (B)=0.60, 95% CI=0.15-2.2, p=0.44, and EXP (B)=0.39, 95% CI=0.10-1.5, p=0.17 respectively), indicating that high IgM titers to OxLDL and to MDA-LDL may be specifically protective among women.

TABLE 1

Basic characteristics of the study group at enrolment. Results are presented as means (SD) or percentage (%) and mg/dL for lipids.

| | Total (N = 226) | Atenolol (N = 115) | Lacidipine (N = 111) |
|---|---|---|---|
| Age (years) | 57.7 (7.8) | 57.6 (7.6) | 57.7 (7.9) |
| Sex (% males) | 50 | 46 | 53 |
| BMI | 26.7 (3.7) | 26.3 (3.3) | 27.1 (3.9) |
| Total cholesterol | 232.4 (37.8) | 233.5 (38.1) | 231.4 (37.4) |
| HDL | 55.6 (27.6) | 56.5 (25.8) | 54.7 (27.6) |
| LDL | 149.4 (37.8) | 149.7 (37.1) | 149.2 (38.6) |
| Trigyclerides | 131.6 (58.2) | 128.6 (57.0) | 134.7 (59.5) |

TABLE 2

Unadjusted prediction of changes in IMT with baseline levels of IgG and IgM autoantibodies to phosphorylcholine (PC).

| Variable | Odds Ratio | (95% CI) Lower | Upper | P |
|---|---|---|---|---|
| | 75th percentile | | | |
| aPC (IgG) | .60 | .32 | 1.1 | .10 |
| aPC (IgM) | .46 | .25 | .85 | .01 |
| aOxLDL (IgG) | 1.2 | .64 | 2.3 | .57 |
| aOxLDL (IgM) | .77 | .41 | 1.4 | .40 |

TABLE 2-continued

Unadjusted prediction of changes in IMT with baseline levels of IgG and IgM autoantibodies to phosphorylcholine (PC).

| Variable | Odds Ratio | (95% CI) Lower | Upper | P |
|---|---|---|---|---|
| aMDA-LDL (IgG) | .80 | .43 | 1.5 | .48 |
| aMDA-LDL (IgM) | .67 | .36 | 1.2 | .18 |
| C-reactive protein | .80 | .43 | 1.5 | .46 |
| | 90th percentile | | | |
| aPC (IgG) | .60 | .25 | 1.4 | .24 |
| aPC (IgM) | .36 | .15 | 0.87 | .024 |
| aOxLDL (IgG) | .94 | .38 | 2.31 | .90 |
| aOxLDL (IgM) | .27 | .11 | .69 | .006 |
| aMDA-LDL (IgG) | .63 | .26 | 1.5 | .30 |
| aMDA-LDL (IgM) | .27 | .11 | .69 | .006 |
| C-reactive protein | .60 | .24 | 1.4 | .24 |

TABLE 3a prediction of changes in MT over a 4-year period using the 75th percentile of aPC IgM autoantibodies at baseline in subjects with established hypertension.

| Variable in the model | Co-efficient (B) | Estimated odds ratio Exp(B) | P | 95% CI Lower | Upper |
|---|---|---|---|---|---|
| Smoking | −.01 | .99 | .95 | .66 | 1.5 |
| Sex | −.05 | .95 | .87 | .54 | 1.4 |
| Total choles-terol | .003 | 1.0 | .45 | .99 | 1.0 |
| Plasma triglyc-erides | −.001 | .99 | .63 | .99 | 1.0 |
| Age (years) | .01 | 1.0 | .59 | .97 | 1.0 |
| Treat-ment (A/L) | −.23 | .79 | .40 | .45 | 1.4 |
| APC IgM | −1.0 | .37 | .0027 | .15 | .89 |

TABLE 3b prediction of changes in IMT over a 4-hyear period using the 90th precentile of aPC IgM autoantibodies in subjects with established hypertension.

| Variable in the model | Co-efficient (B) | Estimated odds ratio Exp(B) | P | 95% CI Lower | Upper |
|---|---|---|---|---|---|
| Smoking | −.02 | .97 | .90 | .65 | 1.5 |
| Sex | −.005 | 1.0 | .98 | .56 | 1.8 |
| Total choles-terol | .003 | 1.0 | .42 | .99 | 1.0 |

TABLE 3b-continued prediction of changes in IMT over a 4-hyear period using the 90th percentile of aPC IgM autoantibodies in subjects with established hypertension.

| Variable in the model | Co-efficient (B) | Estimated odds ratio Exp(B) | P | 95% CI Lower | Upper |
|---|---|---|---|---|---|
| Plasma triglycerides | −.001 | 0.99 | .67 | .99 | 1.0 |
| Age (years) | .003 | 1.0 | .87 | .97 | 1.0 |
| Treatment (A/L) | −.22 | .80 | .43 | .46 | 1.4 |
| aPC IgM | −.77 | .46 | .017 | .24 | .87 |

TABLE 3c

Prediction of changes in IMT over a 4-year period using the 90th percentile with IgM autoantibodies to OxLDL and other risk factors in subjects with established hypertension

| Variable in the model | Coefficient (B) | Estimated odds ratio Exp(B) | P | 95% CI Lower | Upper |
|---|---|---|---|---|---|
| Smoking | −.01 | .99 | .95 | .66 | 1.5 |
| Sex | .001 | 1.1 | .98 | .56 | 1.8 |
| Total cholesterol | .001 | 1.0 | .72 | .99 | 1.1 |
| Plasma triglycerides | −.001 | 1.0 | .71 | .99 | 1.0 |
| Age (years) | .01 | 1.0 | .60 | .97 | 1.1 |
| Treatment (A/L) | −.28 | .77 | .35 | .44 | 1.3 |
| aOxLDL IgM | −1.3 | .26 | .008 | .11 | .72 |

TABLE 3d

Predicition of changes in IMT over a 4-year period using the 90th percentile with IgM autoantibodies to MDA-LDL and other risk factors in subjects with established hypertension

| Variable in the model | Coefficient (B) | Estimated odds ratio Exp(B) | P | 95% CI Lower | Upper |
|---|---|---|---|---|---|
| Smoking | −.07 | 0.93 | .73 | .62 | 1.4 |
| Sex | −.001 | .99 | .99 | .56 | 1.7 |
| Total cholesterol | 0.001 | 1.0 | .78 | .99 | 1.0 |
| Plasma triglycerides | −.001 | .99 | .74 | .99 | 1.1 |
| Age (years) | 0.01 | 1.0 | .54 | .97 | 1.0 |
| Treatment (A/L) | −.27 | .76 | .34 | .44 | 1.3 |
| aMDM-LDL IgM | −1.1 | .31 | .01 | .12 | .79 |

REFERENCES

1. Frostegard J, Ulfgren A K, Nyberg P, Hedin U, Swedenborg J, Andersson U, Hansson G K. Cytokine expression in advanced human atherosclerotic plaques: dominance of pro-inflammatory (Th1) and macrophage-stimulating cytokines. Atherosclerosis. 1999; 145:33-43.
2. Binder C J, Chang M K, Shaw P X, Miller Y I, Hartvigsen K, Dewan A, Witztum J L. Innate and acquired immunity in atherogenesis. Nat. Med. 2002; 8:1218-26.
3. Frostegard J. Autoimmunity, oxidized LDL and cardiovascular disease. Autoimmun Rev. 2002; 1:233-7.
4. Palinski W, Miller E, Witztum J L. Immunization of low density lipoprotein (LDL) receptor-deficient rabbits with homologous malondialdehyde-modified LDL reduces atherogenesis. Proc Natl Acad Sci USA. 1995; 92:821-5.
5. Xu Q, Dietrich H, Steiner H J, Gown A M, Schoel B, Mikuz G, Kaufmann S H, Wick G. Induction of arteriosclerosis in normocholesterolemic rabbits by immunization with heat shock protein 65. Arterioscler Thromb. 1992; 12:789-99.
6. Wu R, de Faire U, Lemne C, Witztum J L, Frostegard J. Autoantibodies to OxLDL are decreased in individuals with borderline hypertension. Hypertension. 1999; 33:53-9.
7. Hulthe J, Wiklund O, Hurt-Camejo E, Bondjers G. Antibodies to oxidized LDL in relation to carotid atherosclerosis, cell adhesion molecules, and phospholipase A(2). Arterioscler Thromb Vasc Biol. 2001; 21:269-74.
8. Karvonen J, Paivansalo M, Kesaniemi Y A, Horkko S. Immunoglobulin M type of autoantibodies to oxidized low-density lipoprotein has an inverse relation to carotid artery atherosclerosis. Circulation. 2003; 108:2107-12.
9. Bergmark C, Wu R, de Faire U, Lefvert A K, Swedenborg J. Patients with early-onset peripheral vascular disease have increased levels of autoantibodies against oxidized LDL. Arterioscler Thromb Vasc Biol. 1995; 15:441-5.
10. Salonen J T, Ylii-Herttuala S, Yamamoto R, Butler S, Korpela H, Salonen R, Nyyssönen K, Palinski W, Witztum J L. Autoantibody against oxidised LDL and progression of carotid atherosclerosis. Lancet. 1992; 339:883-887.

11. Svenungsson E, Jensen-Urstad K, Heimburger M, Silveira A, Hamsten A, de Faire U, Witztum J L, Frostegard J. Risk factors for cardiovascular disease in systemic lupus erythematosus. Circulation. 2001; 104:1887-93.
12. Frostegard J, Wu R, Giscombe R, Holm G, Lefvert A K, Nilsson J. Induction of T-cell activation by oxidized low density lipoprotein. Arterioscler Thromb. 1992; 12:461-7.
13. Stemme S, Faber B, Holm J, Wiklund O, Witztum J L, Hansson G K. T lymphocytes from human atherosclerotic plaques recognize oxidized low density lipoprotein. Proc Natl Acad Sci USA. 1995; 92:3893-7.
14. Berliner J A, Territo M C, Sevanian A, Ramin S, Kim J A, Bamshad B, Esterson M, Fogelman A M. Minimally modified low density lipoprotein stimulates monocyte endothelial interactions. J Clin Invest. 1990; 85:1260-6.
15. Frostegard J, Nilsson J, Haegerstrand A, Hamsten A, Wigzell H, Gidlund M. Oxidized low density lipoprotein induces differentiation and adhesion of human monocytes and the monocytic cell line U937. Proc Natl Acad Sci USA. 1990; 87:904-8.
16. Frostegard J, Haegerstrand A, Gidlund M, Nilsson J. Biologically modified LDL increases the adhesive properties of endothelial cells. Atherosclerosis. 1991; 90:119-26.
17. Fei G Z, Huang Y H, Swedenborg J, Frostegard J. Oxidised LDL modulates immune-activation by an IL-12 dependent mechanism. Atherosclerosis. 2003; 169:77-85.
18. Bochkov V N, Kadl A, Huber J, Gruber F, Binder B R, Leitinger N. Protective role of phospholipid oxidation products in endotoxin-induced tissue damage. Nature. 2002; 419:77-81.
19. Frostegard J, Huang Y H, Ronnelid J, Schafer-Elinder L. Platelet-activating factor and oxidized LDL induce immune activation by a common mechanism. Arterioscler Thromb Vasc Biol. 1997; 17:963-8.
20. Heery J M, Kozak M, Stafforini D M, Jones D A, Zimmerman G A, McIntyre T M, Prescott S M. Oxidatively modified LDL contains phospholipids with platelet-activating factor-like activity and stimulates the growth of smooth muscle cells. J Clin Invest. 1995; 96:2322-30.
21. Subbanagounder G, Leitinger N, Shih P T, Faull K F, Berliner J A. Evidence that phospholipid oxidation products and/or platelet-activating factor play an important role in early atherogenesis: in vitro and In vivo inhibition by WEB 2086. Circ Res. 1999; 85:311-8.
22. Harnett W, Harnett M M. Phosphorylcholine: friend or foe of the immune system? Immunol Today. 1999; 20:125-9.
23. Shaw P X, Horkko S, Chang M K, Curtiss L K, Palinski W, Silverman G J, Witztum J L. Natural antibodies with the T15 idiotype may act in atherosclerosis, apoptotic clearance, and protective immunity [see comments]. J Clin Invest. 2000; 105:1731-40.
24. Binder C J, Horkko S, Dewan A, Chang M K, Kieu E P, Goodyear C S, Shaw P X, Palinski W, Witztum J L, Silverman G J. Pneumococcal vaccination decreases atherosclerotic lesion formation: molecular mimicry between *Streptococcus pneumoniae* and oxidized LDL. Nat. Med. 2003; 9:736-43.
25. Zanchetti A, Bond M G, Hennig M, Neiss A, Mancia G, Dal Palu C, Hansson L, Magnani B, Rahn K H, Reid J, Rodicio J, Safar M, Eckes L, Ravinetto R. Risk factors associated with alterations in carotid intima-media thickness in hypertension: baseline data from the European Lacidipine Study on Atherosclerosis. J Hypertens. 1998; 16:949-61.
26. Zanchetti A, Bond M G, Hennig M, Neiss A, Mancia G, Dal Palu C, Hansson L, Magnani B, Rahn K H, Reid J L, Rodicio J, Safar M, Eckes L, Rizzini P. Calcium antagonist lacidipine slows down progression of asymptomatic carotid atherosclerosis: principal results of the European Lacidipine Study on Atherosclerosis (ELSA), a randomized, double-blind, long-term trial. Circulation. 2002; 106:2422-7.

Study Showing Protective Effect of aPC

In an observational study from Malmö (the Malmö Diet and Cancer Study), about 6000 out of 30000 subjects from the cohort were recruited for extensive cardiovascular investigations, including non-invasive assessment of subclinical atherosclerosis through ultrasound measurements of the carotids. In addition, additional cardiovascular risk factors were measured at baseline. These subjects have been followed for over 10 years with regard to the occurrence of new events of cardiovascular diseases (myocardial infarction, chronic coronary heart disease, atherotrombotic stroke). In order to assess the relative risks (calculated as relative hazards) with 95% confidence intervals, nested-case-control analyses (3 controls per case) were undertaken for low levels of antibodies against phosphorylcholine (aPC-IgM). There were in total 145 CVD cases (mainly myocardial infarction (MI) and ischemic stroke) and 400 age and sex-matched controls. The cutoff level for aPC was 307 for the tenth percentile of aPC levels. There were in total 20 CVD cases with aPC levels below the tenth percentile (14%), and 34 controls (9%), corresponding to a relative hazard of 1.9 (95% CI 1.1-4.3). The corresponding number of male CVD cases below the tenth percentile of aPC was 16 (19%), and 25 control patients below this level (11%), corresponding to a relative hazard of 1.9 (95% CI 1.1-3.5). The number of female cases was too low to yield robust information on relative risks (see Tables 1 and 2). The results suggest that low aPC levels are predictive for the occurrence of cardiovascular disease in healthy subjects, and could act as markers for cardiovascular diseases.

TABLE 1

Descriptive statistics for aPC (<$10^{th}$ percentile)

| | | SEX | | | | | |
|---|---|---|---|---|---|---|---|
| | | Males | | Females | | All | |
| Below $10^{th}$ pct | | Case | Control | Case | Control | Case | Control |
| No | n | 68 | 206 | 57 | 160 | 125 | 366 |
| | % | 81 | 89 | 93 | 95 | 86 | 92 |
| Yes | N | 16 | 25 | 4 | 9 | 20 | 34 |
| | % | 19 | 11 | 7 | 5 | 14 | 9 |

TABLE 2

Univariate analysis of the influence of aPC (<$10^{th}$ percentile) on CVD by conditional logistic regression for all patients, males and females, respectively.

| | Variable | p-value | Hazard ratio | 95% Hazard Ratio Confidence Limits | |
|---|---|---|---|---|---|
| All patients | aPC | 0.0308 | 1.939 | 1.063 | 3.536 |
| Males | aPC | 0.0262 | 2.181 | 1.097 | 4.338 |
| Females | aPC | 0.6556 | 1.331 | 0.379 | 4.676 |

Effects of aPC

Introduction

By use of columns which are preabsorbed with PC-BSA, PC-KLH or Pneumococcal vaccine (Statens Serum Institute, Denmark), we extract antibodies with reactivity against these compounds. Levels of aPC IgG are raised in at least the two first of these. Small amounts of IgM may be extracted out of IVIG and then also run through the columns preabsorbed with the abovementioned antigens. Through this method we can obtain polyclonal human aPC of IgG and IgM subclass. Protein measurement indicates that aPC IgM levels of 0.5 mg/ml could be extracted. Using these antibodies we can test their functional properties using in vitro models:

1. Can preincubation of increasing concentrations of aPC IgM with oxidized LDL decrease binding and uptake in monocyte/macrophage cell line, THP1? Test systems with confocal microscopy and/or FACS can be used.
2. Can preincubation of increasing concentrations of aPC IgM with normal IgM as control, with PAF, lysophosphatidylcholine (LPC) inhibit induction of adhesion molecules ICAM on endothelial cells by these lipids? Also other cytokines can be tested using a commercial kit (several different cytokines; BioSource). Tests can make use of FACScan.

Cell Culture

Cryopreserved pooled HUVECs at passage 2 were purchased from Cascade Biologics, Inc. (Portland, Oreg., USA). Cultures were maintained in EGM™ phenol red-free medium (Clonetics, San Diego, Calif., USA), containing 2% of fetal bovine serum and supplements. The cells were incubated in 75 $cm^2$ flasks (TPP, AG, Trasadingen, Switzerland) at 37° C. under humidified 5% $CO_2$ conditions.

All experiments were performed at passage 3 to 4. Cells were seeded at $2\times10^4$ cells/ml density in 12-well plates (NUNC, Inc, Naperville, Ill., USA) for flow cytometry analysis. After allowing 12-24 hours for attachment the cells were made quiescent in SFM for at least 12 hrs prior to treatment.

Monocytic cell line THP-1 was from AT&T (USA). Cells were maintained in RPMI with 10% FCS.

Preparation of aPC

Total IgM or IgG fraction was separated from commercially available pooled human immunoglobulin (Gammagard®) at 50 mg/ml using HiTrap IgM or IgG columns (Amersham Biosciences). Antibodies against phosphorylcholine (PC) were eluted after loading IgM or IgG fraction on NHS-Sepharose columns coupled to PC conjugated either to keyhole limpet protein (KLH) (1 or 5 mg/ml) or to bovine serum albumin (BSA) (1 mg/ml), followed by BSA-only column. PC-BSA (Phosphorylcholine-Bovine Serum Albumin) and PC-KLH was purchased from Biosearch Technologies, INC (Ca, USA). Eluted fractions were buffer-exchanged on PD-10 columns and concentrated with Millipore Centricone® devices. Procedures were performed according to instructions given by manufacturers. The concentration of IgM aPC prepared was typically 50 g/ml, and the concentration of IgG aPC was typically 30 g/ml.

Scavenger Binding and Uptake of oxLDL by THP-1 Derived Macrophages

Oxidized LDL (oxLDL) is prepared as described by incubation with copper ions. First, oxLDL is labeled with Dil (Dil-(1,1'-dioctadecyl-3,3,3',3'-tetramethylindocarbocyanine perchlorate; Molecular Probes, Inc)) and diluted in Saline-EDTA buffer to 1 mg/ml. After that, 2 ml lipoprotein-deficient serum is added for 1 mg of oxLDL and then filtered (0.45 um). 50 ul Dil (3 mg/ml) in DMSO is added for 1 mg oxLDL and the mixture is incubated 15 h, 37° C. and then dialyzed against several changes of saline-EDTA for 6 h. After this the mixture is 0.45 um filtered again.

Uptake of the oxLDL is studied with fluorescence/confocal microscopy. THP-1 cells as models for monocytes/macrophages are grown overnight on slide chamber. (medium: DMEM/10% FBS/Glu/PEST)

3× wash with DMEM medium without FBS

Incubated with oxLDL-DiO 5 ug/ml (SFM medium) 6 h.

The cells washed with 0.2% BSA-PBS 5×, PBS 1×

Macrophage nucleus staining: the cells were incubated with 1 ug/ml bisbenzimide 10' and wash with PBS 3×.

Fix and mount: the cells were then fixed with 4% paraformaldehyde in PBS for 30', PBS 3×, to finally, after 1 drop of mounting gel. The slides were covered with cover slip.

Annexin V binding to endothelial cells

Heparin-preserved plasma with high capacity to inhibit Annexin V binding was added to HUVECs monolayer at concentration of 10% in SFM. After 24 hrs cells were harvested with Cell Dissociation Solution (CDS; Sigma-Aldrich, St. Louis, Mo., USA) and carefully pooled with supernatants, to exclude selective loss of detached floating cells, centrifugation at 1200 rpm for 7 min followed. After resuspension in 100 μl of annexin V-binding buffer (Molecular Probes Inc, Eugene, Oreg., USA) samples were stained with 2 μl 5 mg/ml annexin V-FITC (Molecular Probes) and incubated for 15 min on ice. Shortly before acquisition 1 mg/ml of propidium iodide (PI; a vital dye; R&DSystems Europe Ltd, Abingdon, UK) was added. Analysis was performed as described above.

Statistical Analysis

The statistics were computed using Stat View software, SAS Institute AB, Göteborg, Sweden. Skewed continuous variables were logarithmically transforme. Study groups were compared using ANOVA for continuous variables and Chi square for categorical variables. Fischer's PLSD was used as post hoc test. Correlation coefficients were calculated using Simple regression or for not normally distributed variables Spearman's rank correlation. The significance level was set at $p<0.05$.

Results

Measurements of Annexin V Binding to Endothelial Cells

The frequency of HUVECs positive for annexin V staining was determined either as percentage of annexin $V^+/PI^-$ cells on a bivariate dot plot or percentage of annexin $V^+$ cells based on a histogram. Annexin V-binding to HUVECs in the presence of serum known to decreased binding and preincubated with IVIG was determined. Preincubation with IVIG could restore binding of Annexin, indicating that antibodies present in IVIG could neutralize binding (FIG. 4).

APC-BSA and aPC-KHL were both associated significantly in SLE-patients with a history of CVD with Annexin V binding to EC ($r=-0.45$; $p=0.02$ and $r=0.42$ and $p=0.03$ respectively). aPC were determined as described above.

Effect on oxLDL Uptake in Macrophages by aPC aPC of IgM and IgG subclass, extracted from IVIG as indicated were preincubated with oxLDL indicated (fig 3). We used total IgM as control for aPC IgM (macrophage+Dil-oxLDL+IgM) and effect on macrophage uptake. The total percentage of positive staining cells is 46.62%, indicating that IgM per se does not have the inhibitory effects that aPC has. IgM was bought from SIGMA, and is purified human IgM is produced by precipitation and gel filtration techniques using normal human serum as the starting material. The immunoglobulin is determined to be at least 95% pure.

Effect of aPC on ICAM-Induction in Endothelial Cells

PAF was incubated with EC at the indicated concentrations. As demonstrated in FIG. 5 this lipid could induce a significant increase in ICAM-expression. aPC of IgM subclass, extracted from IVIG as indicated were preincubated with these lipids as indicated (FIG. 5).

Correlations Between aPC and Other Risk Markers in ELSA Study (226 Individuals with Hypertension as Described Previously.

aPC IgM was associated with two other protection factors, HSP 70 and HDL, as indicated in Table 4. There was also a weak albeit significant association with TNF, a marker of inflammation and a proatherogenic cytokine.

TNF is an important pro-inflammatory cytokine and TNF levels negatively associated with aPC IgM levels. The association is weak, but significant.

HSP 70 is a novel protection factor recently described by us and others. There is a clearly positive association. Also HSP60, which is a weaker protection factor, is associated.

HDL is a well known "good" cholesterol, with anti-inflammatory properties. It is associated significantly with aPC IgM.

| | ANTPCIGG | ANTPCIGM |
|---|---|---|
| Spearman's rho ANTPCIGG | 1,000 | ,245 |
| Correlation Coefficient | | |
| Sig. (2-tailed) | , | ,000 |
| N | 220 | 220 |
| ANTPCIGM | ,245 | 1,000 |
| Correlation Coefficient | | |
| Sig. (2-tailed) | ,000 | , |
| N | 220 | 220 |
| HDL | ,008 | ,233 |
| Correlation Coefficient | | |
| Sig. (2-tailed) | ,906 | ,001 |
| N | 206 | 206 |
| TNFA | −,012 | −,136 |
| Correlation Coefficient | | |
| Sig. (2-tailed) | ,863 | ,044 |
| N | 220 | 220 |
| HSP60 | ,138 | ,279 |
| Correlation Coefficient | | |
| Sig. (2-tailed) | ,047 | ,000 |
| N | 209 | 209 |
| HSP70 | ,157 | ,356 |
| Correlation Coefficient | | |
| Sig. (2-tailed) | ,022 | ,000 |
| N | 213 | 213 |

**Correlation is significant at the .01 level (2-tailed).

*Correlation is significant at the .05 level (2-tailed).

The invention claimed is:

1. A method for immunization and treatment of a human against an atherosclerotic related disease selected from the group consisting of cardiovascular disease, stroke myocardial infarction and/or peripheral artery disease, the method comprising the step of administering to the human a pharmaceutical composition comprising a monoclonal antibody preparation with specificity to a phosphorylcholine conjugate, wherein said monoclonal antibody preparation comprises monoclonal antibodies with specificity for a phosphorylcholine conjugate.

2. The method of claim 1 wherein the composition is administered by injection.

3. The method of claim 1, wherein the phosphorylcholine conjugate comprises phosphorylcholine linked to a carrier via a spacer.

4. The method according to claim 1, wherein the phosphorylcholine conjugate comprises phosphorylcholine linked to a protein carrier, optionally via a spacer.

5. The method according to claim 4, wherein the protein carrier is KLH (keyhole limpet hemocyanin) or human serum albumin (HSA).

6. The method according to claim 3, wherein the phosphorylcholine conjugate comprises phosphorylcholine linked to a latex bead, optionally via a spacer.

7. A method of prophylactic or therapeutic treatment of a human being suffering from or facing the risk of developing an atherosclerotic related disease selected from the group consisting of cardiovascular disease, stroke, myocardial infarction and/or peripheral artery disease, whereby a therapeutically effective amount of monoclonal antibody preparation with specificity to a phosphorylcholine conjugate is administered, wherein said monoclonal antibody preparation comprises monoclonal antibodies with specificity for a phosphorylcholine conjugate.

8. The method of claim 7, wherein the human that is immunized and treated is a human patient that has been determined to be at risk of developing or progression of cardiovascular disease, myocardial infarction, stroke and/or peripheral artery disease by a method comprising assessing the human patient's level of antibodies reactive with a phosphorylcholine conjugate, wherein the level of antibodies reactive with a phosphorylcholine conjugate correlates negatively with the risk of developing or progression of cardiovascular disease in a healthy human patient.

9. The method of claim 8, wherein the patient has been determined to be at risk of developing or progression of cardiovascular disease.

10. The method of claim 9 wherein the cardiovascular disease is atherosclerosis.

11. The method of claim 8, wherein the human patient has been determined to be at risk of developing or progression of cardiovascular disease by a method comprising assessing the human patient's level of IgM antibodies reactive with a phosphorylcholine conjugate.

12. The method of claim 8, wherein the human patient has been determined to be at risk of developing or progression of cardiovascular disease by a method comprising assessing the human patient's level of IgG antibodies reactive with a phosphorylcholine conjugate.

13. The method of claim 11 wherein the cardiovascular disease is atherosclerosis.

14. The method of claim 12 wherein the cardiovascular disease is atherosclerosis.

15. The method of claim 8, wherein the patient has been determined to be at risk of developing or progression of myocardial infarction.

16. The method of claim 15, wherein the human patient has been determined to be at risk of developing or progression of myocardial infarction by a method comprising assessing the human patient's level of IgM antibodies reactive with a phosphorylcholine conjugate.

17. The method of claim 8, wherein the human patient has been determined to be at risk of developing or progression of myocardial infarction by a method comprising assessing the human patient's level of IgG antibodies reactive with a phosphorylcholine conjugate.

18. The method of claim 8, wherein the patient has been determined to be at risk of developing or progression of peripheral artery disease.

19. The method of claim 15, wherein the human patient has been determined to be at risk of developing or progression of peripheral artery disease by a method comprising assessing the human patient's level of IgM antibodies reactive with a phosphorylcholine conjugate.

20. The method of claim 8, wherein the human patient has been determined to be at risk of developing or progression of peripheral artery disease by a method comprising assessing the human patient's level of IgG antibodies reactive with a phosphorylcholine conjugate.

* * * * *